United States Patent [19]

Spitzer et al.

[11] 3,988,325

[45] Oct. 26, 1976

[54] 7-CARBOXY OR 2,2,2-TRICHLOROETHOXY CARBONYL-CEPHALOSPORINS

[75] Inventors: Wayne A. Spitzer, Indianapolis; Ian G. Wright, Greenwood, both of Ind.

[73] Assignee: Eli Lilly and Company, Indianapolis, Ind.

[22] Filed: July 3, 1972

[21] Appl. No.: 268,367

[52] U.S. Cl. .............................. 260/243 C; 424/246
[51] Int. Cl.² ............................................. C07D 501/60
[58] Field of Search ................................. 260/243 C

[56] References Cited
UNITED STATES PATENTS

| | | | |
|---|---|---|---|
| 3,709,880 | 1/1973 | Goegelman et al. | 260/243 C |
| 3,840,533 | 10/1974 | Dolfini et al. | 260/243 C |

FOREIGN PATENTS OR APPLICATIONS

| | | |
|---|---|---|
| 71/3229 | 1/1972 | South Africa |

*Primary Examiner*—Nicholas S. Rizzo
*Assistant Examiner*—Jose Tovar
*Attorney, Agent, or Firm*—William B. Scanlon; Everet F. Smith

[57] ABSTRACT

6-APA, 7-ACA and 7-ADCA esters are reacted with benzaldehyde, acetophenone or substituted derivatives thereof providing imines which react in the presence of a strong base such as sodium hydride or lithium diisopropyl amide with a $C_2$–$C_5$ alkanoyl halide, 2,2,2-trichloroethoxycarbonyl chloride, a benzoyl halide, a $C_1$–$C_4$ alkoxycarbonyl chloride or a methoxymethyl halide to afford $C_6$ and $C_7$ substituted β-lactam imines via acylation or methoxymethylation. The β-lactam substituted imines are reacted with a carbonyl reagent, e.g. Girard's reagent T to provide a $C_6$ substituted 6-APA ester or a $C_7$ substituted 7-ACA or 7-ADCA ester which is acylated to provide a 6-acylamido-6-substituted penicillin or a 7-acyl-amide-7-substituted cephalosporin.

3 Claims, No Drawings

7-CARBOXY OR 2,2,2-TRICHLOROETHOXY CARBONYL- CEPHALOSPORINS

BACKGROUND OF THE INVENTION

This invention relates to penicillin and cephalosporin antibiotics. In particular it relates to 6-substituted-6-acylamidopenicillanic acids, 7-substituted-7-acylamidocephalosporanic acids, 7-substituted-7-acylamidodeacetoxycephalosporanic acids, the esters and pharmaceutically acceptable salts of the foregoing acids, and to a process and intermediates useful in the preparation thereof.

Heretofore many semi-synthetic penicillins and cephalosporin antibiotics have been prepared by the acylation of 6-aminopenicillanic acid (6-APA), 7-aminocephalosporanic acid (7-ACA) and 7-aminodeacetoxycephalosporanic acid (7-ADCA) with a wide variety of acyl groups. In addition, many novel cephalosporin antibiotics have been synthesized by substitution reactions involving the methylene group in the 3-position of the dihydrothiazene ring of the cephalosporin nucleus. However, the literature contains scant information on penicillins and cephalosporin antibiotics having a substituent attached to one of the carbon atoms of the β-lactam ring.

Since the prediction by J. L. Strominger and D. J. Tipper, Amer. J. Med. 39, 708 (1965), that 6-methyl penicillins and 7-methyl cephalosporins should have enhanced microbiological activity and the recent discovery of the 7-methoxycephalosporins obtained from the fermentation of Streptomycete organisms by R. Nagarajan, et al., J. Amer. Chem. Soc., 93, 2308 (1971), considerable interest has developed in the synthesis of β-lactam antibiotics having a substituent α to the β-lactam carbonyl of the penicillin and cephalosporin antibiotics.

SUMMARY

6-Acylamido-6-substituted penicillanic acids, 7-acylamido-7-substituted cephalosporanic acids and 7-acylamido-7-substituted deacetoxycephalosporanic acids and esters thereof, wherein the 6- and 7-substituents are $C_2$–$C_5$ alkanoyl, $C_1$–$C_4$ lower alkoxycarbonyl, 2,2,2-trichloroethoxycarbonyl, carboxy, benzoyl, or methoxymethyl are prepared by the acylation or methoxyalkylation of an imine formed with an ester of 6-APA, 7-ACA or 7-ADCA and an aromatic aldehyde or an aromatic ketone.

The substitution of the imine ester on the β-lactam carbon atom is carried out by generating in a cold anhydrous medium the anionic form of the imine ester with a strong base such as sodium hydride or lithium diisopropyl amide and shortly thereafter reacting the anion with the desired acylating agent to provide the $C_6$ or $C_7$ substituted penicillin or cephalosporin as the imine ester derivative. The substituted imine ester is then reacted with a carbonyl reagent such as Girard's reagent T, sodium bisulfite or aminooxyacetic acid to effect the cleavage of the imine group and provide a 6-amino-6-substituted penicillanic acid ester or a 7-amino-7-substituted deacetoxycephalosporanic acid ester.

The substituted penicillin and cephalosporin amino nuclei are then acylated in the conventional manner to provide the 6- and 7-acylamido derivatives thereof. Removal of the ester group provides the substituted β-lactam compounds of the invention as the free acids.

The substituted β-lactam compounds provided by the process of the invention possess antibiotic activity and are useful in inhibiting the growth of and combatting infections due to gram-positive microorganisms.

DETAILED DESCRIPTION

The 6-substituted penicillanic, 7-substituted cephalosporanic and deacetoxycephalosporanic acids provided by this invention are represented by the following Formula 1.

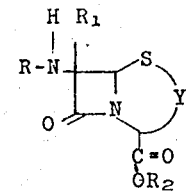

wherein R is hydrogen, $C_2$–$C_7$ alkanoyl, benzoyl, $C_1$–$C_4$ lower alkylbenzoyl, halobenzoyl, $C_1$–$C_4$ lower alkoxybenzoyl, nitrobenzoyl, hydroxybenzoyl, or a group of the formula

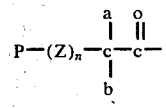

wherein P is phenyl, $C_1$–$C_4$ lower alkylphenyl, halophenyl, $C_1$–$C_4$ lower alkoxyphenyl, nitrophenyl, hydroxyphenyl, or a heteromonocyclic radical containing O, S, and/or N;
Z is O or S;
n is 0 or 1;
a is hydrogen or $C_1$–$C_3$ lower alkyl;
b is hydrogen, $C_1$–$C_3$ lower alkyl, hydroxy, amino, or protected amino;
$R_1$ is $C_2$–$C_5$ alkanoyl, benzoyl, 2,2,2-trichloroethoxycarbonyl, carboxy, $C_1$–$C_4$-alkoxycarbonyl, or methoxy-methyl;
$R_2$ is hydrogen, or a carboxylic acid protecting ester forming group;

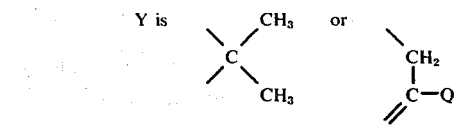

wherein Q is methyl or acetoxymethyl.

In the foregoing definition of the compounds provided by the present invention the term, "$C_2$–$C_7$ alkanoyl", refers to acetyl, propionyl, butyryl, iso-butyryl, pivaloyl, valeryl, n-hexanoyl, n-heptanoyl and like groups. The term, "$C_1$–$C_3$ lower alkyl", has reference to methyl, ethyl, n-propyl, and iso-propyl. The term, "$C_1$–$C_4$ lower alkylbenzoyl", refers to 4-methylbenzoyl, 4-iso-propylbenzoyl, 4-t-butylbenzoyl, 3,4-dimethylbenzoyl, 3-ethylbenzoyl, 2-methylbenzoyl and the like; "$C_1$–$C_4$ lower alkoxybenzoyl" refers to 2,6-dimethoxybenzoyl, 4-ethoxybenzoyl, 3-iso-propoxybenzoyl, 3-ethoxy-4-methoxybenzoyl, 3,4-dimethoxybenzoyl and the like; "nitrobenzoyl" refers to 4-nitrobenzoyl, 3- nitrobenzoyl and the like; "halobenzoyl" is defined herein as the mono or dihalogenated benzoyl groups such as 4-fluorobenzoyl, 3-chlorobenzoyl, 3,4-dichlorobenzoyl, 3-bromobenzoyl and the like; and "hydroxybenzoyl" is defined by such groups as 4-hydroxybenzoyl, 3,4-dihydroxybenzoyl, 2,4-dihydroxybenzoyl, 3-hydroxybenzoyl and the like.

The term "heteromonocyclic radical containing O, S, and/or N" as employed herein refers to the 5 and 6 membered heterocyclic groups of one ring such as 2-thienyl, 3-thienyl, 2-furyl, 3-furyl, 2-oxazolyl, 2-thiazolyl, triazinyl, tetrazolyl, 2-imidazolyl, 1,3,4-oxadiazolyl, 1,3,4-thiadiazolyl, 2-pyridyl, 3-pyridyl, pyrimidyl, pyrazinyl, 3-pyrryl, pyranyl, piperidyl, and the like.

The term "protected amino", refers to an amino group substituted by one of the commonly employed amino blocking groups such as t-butyloxycarbonyl, benzyloxycarbonyl, 2,2,2-trichloroethoxycarbonyl, phthaloyl and like groups.

The term, "a carboxylic acid protecting ester forming group", refers to the ester forming groups commonly employed to protect or block the carboxylic acid function of the penicillins and cephalosporins while reactions involving other functional sites of the antibiotics are carried out. Such groups are characterized by their ease of removal by hydrolytic or hydrogenolytic methods. Examples of such ester forming groups are t-butyl, benzyl, 4-methoxybenzyl, 3,5-dimethoxybenzyl, 4-nitrobenzyl, diphenylmethyl (benzhydryl), phenacyl, 2,2,2-trichloroethyl and tetrahydropyranyl. The function of such groups in the present process is merely to protect the reactive carboxylic acid group and to prevent its interference by competitive reaction. The nature of such ester forming groups is not critical in the present invention so long as the ester formed therewith is stable under the process conditions described hereinafter.

Illustrative of the groups represented by R in Formula I are the following: phenylacetyl, phenoxyacetyl, benzoyl, 2,6-dimethoxybenzoyl, 4-nitrophenylacetyl, 3-hydroxyphenylacetyl, 4-methylphenoxyacetyl, 2-thienylacetyl, 2-furylacetyl, 3-pyridylacetyl, 2-oxazolylacetyl, 2-thiazolylacetyl, 2,2-dimethylphenacylacetyl, mandeloyl, 3-hydroxymandeloyl, phenylglycyl, 4-chlorophenylacetyl, phenylmercaptoacetyl, 2-thienylmercaptoacetyl, 2-pyranylacetyl, 2-pyridylacetyl, 2-oxazolylacetyl, 3-furylacetyl, 2-(1,3,4-thiadiazolyl)acetyl, 4-bromophenylmercaptoacetyl, 2-imidazolylacetyl, 5-pyrimidylacetyl, 3,4-dichlorophenylacetyl, 4-hydroxyphenylmercaptoacetyl and like acyl groups.

The 6-substituted penicillins and the 7-substituted cephalosporins represented by the Formula I are prepared by reacting an ester of 6-aminopenicillanic acid, 7-aminocephalosporanic acid or 7-aminodeacetoxycephalosporanic acid with an aromatic aldehyde or an acetophenone to provide a 6-iminopenicillanic acid ester or a 7-iminocephalosporin ester.

The imine is then reacted in an inert solvent with a strong base such as sodium hydride to generate, in situ, an anionic form of the imine which is then acylated by adding to the reaction mixture the desired acyl halide. Following the acylation of the imine, the substituted imine is then reacted with a carbonyl reagent to effect the removal of the aromatic aldehyde or acetophenone which forms a derivative with the carbonyl reagent, and to provide the 6-amino-6-substituted penicillanic acid ester or the 7-amino-7-substituted cephalosporin ester of the Formula I where R is hydrogen.

The free amino group of the substituted penicillin or cephalosporin ester is then acylated with the desired acyl moiety to provide a compound of the Formula I where R is other than hydrogen.

According to the process of this invention an aromatic carbonyl compound represented by the formula

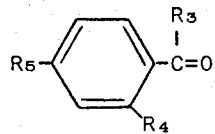

wherein $R_3$ is hydrogen or methyl and $R_4$ and $R_5$ are the same or different and are hydrogen, nitro, chloro or bromo; is reacted with an ester of the penicillin or cephalosporin nucleus represented by the formula

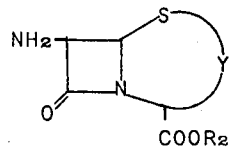

wherein Y and $R_2$ have the same meanings as defined in Formula 1; to provide the imine derivative of the nucleus represented by the following Formula II.

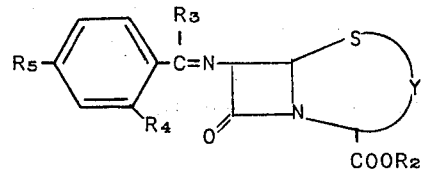

II wherein $R_2$, $R_3$, $R_4$, $R_5$ and Y have the same meanings as previously defined.

The preparation of the imine is carried out in an inert, dry solvent at a temperature between about 25° and 75° C. Solvents which can be employed are the halogenated hydrocarbons such as dichloromethane or chloroform, esters such as ethyl acetate or amyl acetate, the lower alcohols, such as methanol or ethanol or any unreactive solvent in which the amino β-lactam compound and the aromatic carbonyl compound are at least partially soluble over the reaction temperature range.

Generally, the amino β-lactam compound is dissolved in the dry solvent and an equivalent amount of the benzaldehyde or acetophenone is added with stirring. The imines formed with the more reactive aldehydes generally precipitate from the reaction mixture and can be isolated from the mixture by filtration and can be purified by recrystallization. Those imines which do not form as a precipitate can be recovered from the reaction mixture by first evaporating the solvent from the reaction mixture and obtaining the imine from the residue by crystallization from a suitable solvent.

Representative aromatic carbonyl compounds which can be used in the preparation of the imines are benzaldehyde, p-nitrobenzaldehyde, p-chlorobenzaldehyde, 2,4-dibromoacetophenone, p-nitroacetophenone and like benzaldehydes and acetophenones. p-Nitrobenzaldehyde is a preferred compound in the preparation of the imine and likewise in the process for the preparation of the compounds of the invention. p-Nitrobenzaldehyde reacts readily with the amino β-lactam compound to form the imine at a temperature of about 25° C.

Illustrative of the 6-imino penicillanic acid esters and the 7-imino cephalosporin esters provided by this invention and which are useful intermediates in the preparation of the compounds of Formula 1 are the following:

2,2,2-trichloroethyl N-benzylidene-6-aminopenicillanate, 2,2,2-trichloroethyl N-benzylidene-7-aminocephalosporanate, 2,2,2-trichloroethyl N-benzylidene-7-aminodeacetoxycephalosporanate, 2,2,2-trichloroethyl N-(p-nitrobenzylidene)-7-aminocephalosporanate, 4-methoxybenzyl N-(p-nitrobenzylidene)-6-aminopenicillanate, t-butyl N-(p-nitrobenzylidene)-7-aminocephalosporanate, benzyl N-(2,4-dichlorobenzylidene)-7-aminodeacetoxycephalosporanate, benzyl, N-(p-nitrobenzylidene)-6-aminopenicillanate, p-nitrobenzyl N-(p-nitrobenzylidene)-7-aminodeacetoxycephalosporanate, benzhydryl N-(4-chlorobenzylidene)-7-aminocephalosporanate, benzyl N-(2,4-dibromobenzylidene)-6-aminopenicillanate, 2,2,2-trichloroethyl N-(α-methyl-2,4-dichlorobenzylidene)-6-aminopenicillanate, 2,2,2-trichloroethyl N-(α-methylbenzylidene)-7-amino-deacetoxycephalosporanate, and the like.

The intermediate imines are characterized by their elemental analysis, infrared spectra, ultraviolet absorption spectra, mass spectra and nuclear magnetic resonance spectra.

The imine of the Formula II is then reacted in an inert anhydrous solvent in the presence of a strong base, B$^-$, with the desired acylating agent, R$_1$-X, to provide the 6-imino-6-substituted β-lactam compound represented by the Formula III as illustrated by the following reaction scheme.

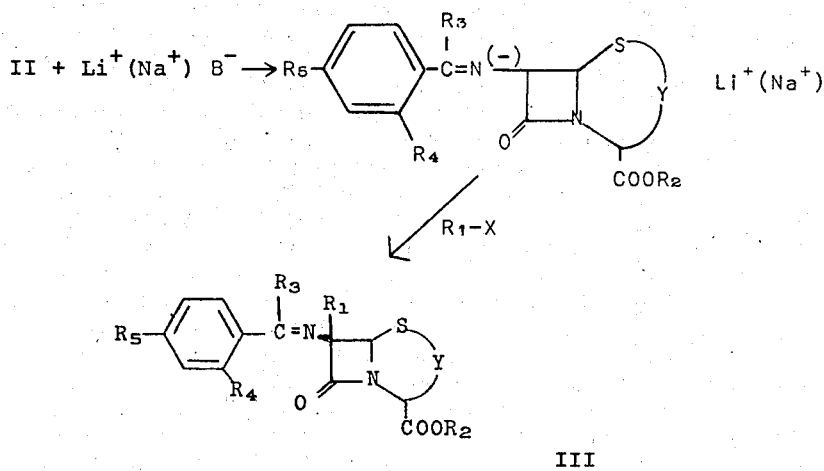

As illustrated above, the β-lactam substitution reaction is carried out by first generating in situ an anionic form of the imine with a strong base and thereafter reacting the anionic form with the desired acylating agent.

Strong bases which can be employed to generate the anion of II in the present reaction are sodium hydride and the lithium amides formed with highly hindered secondary amines as for example, lithium diisopropyl amide, lithium 2,2,6,6-tetramethylpiperidine amide, and lithium t-butyl-t-amyl amide. Sterically hindered carbanions, such as t-butyl lithium can also be employed as the anion generating base. In general, bases which have a sufficient base strength to abstract the C$_6$ proton of a penicillin or the C$_7$ proton of a cephalosporin and which at the same time are poor nucleophilic displacement agents can be employed as bases in the present process.

When sodium hydride is employed as the base the reaction is carried out at a temperature between about −10° and 5° C. Solubility factors deter the use of sodium hydride as the strong base at temperatures much below −10° C. The lithium amides, which are prepared by the reaction of the secondary amine with n-butyl lithium, can be employed at temperatures of about −80° C. to about 0° C. Sodium hydride is desirably employed as a dispersion in purified dimethylformamide (DMF) and preferably spectral grade DMF. The desired base is employed in an amount slightly in excess of a molar equivalent, for example, 1.1 molar equivalents of the imine employed. When a lithium amide is employed as the strong base in the present process, tetrahydrofuran (THF) is a desirable solvent. Also, mixtures of THF and DMF can be employed. Other ethers such as dioxane and dimethoxyethane which are inert under the process conditions can be employed with lithium diisopropyl amide. The reaction is carried out under essentially anhydrous conditions.

The substituting reactant is represented by the general formula R$_1$-X, wherein R$_1$ is C$_2$-C$_5$ alkanoyl, benzoyl, 2,2,2-trichloroethoxycarbonyl, C$_1$-C$_4$ alkoxycarbonyl or methoxymethyl; and X is chloro or bromo. Representative of the reactants, $R_1$-X, are the acylating agents acetyl chloride, propionyl chloride, pivaloyl chloride, n-butyryl bromide, n-valeryl bromide, benzoyl chloride, benzoyl bromide and the like; the haloformates such as methyl chloroformate, ethyl chloroformate, n-butyl chloroformate and the like; 2,2,2-trichloroethoxycarbonyl chloride, and the methoxymethylating agent, methoxymethyl chloride.

The reactant, $R_1$-X, is employed in an equivalent amount or an amount slightly in excess of one equivalent.

The reaction is performed in the following manner. A sodium hydride dispersion in DMF containing 1.1 equivalents of sodium hydride is cooled in the reaction vessel to a temperature of about −5° C. and the substitution reagent, $R_1$-X, is added to the dispersion. With stirring, a solution of the imine prepared as described above in DMF is added rapidly by dropwise addition to the dispersion. The reaction mixture is stirred at the reaction temperature for about 15 to about 30 minutes during which time the reaction is generally complete. The reaction mixture is neutralized and diluted with water and the reaction product mixture is recovered by extraction with a suitable solvent such as ethyl acetate.

Alternatively when a lithium amide such as lithium diisopropyl amide is employed as the base a solution of the amide in a solvent such as tetrahydrofuran is cooled to a temperature between about −80° C. and about 0° C. A solution of the imine in tetrahydrofuran is then added with stirring to the basic solution. Thereafter the acylating agent, $R_1$-X, is added rapidly by dropwise addition to the anionic form of the imine which exists in situ. The reaction mixture develops a dark coloration as the anion is generated. The color varies from a dark brown or dark green color depending on the particular imine employed. Imines formed with p-nitrobenzaldehyde characteristically impart a deep blue coloration to the reaction mixture as the anionic form of the imine is generated. As the acylating reagent, $R_1$-X is added to the reaction mixture the color fades and eventually disappears when the reaction is complete.

In the preparation of a compound of the Formula I according to the process of this invention the substituted imine ester prepared as described above need not be isolated and purified for use in the succeeding process step. The crude substituted imine is suitable for reacting with an aldehyde or ketone agent to effect cleavage of the imine as described below.

The amount of the desired substituted imine ester present in the crude reaction mixture can be determined by thin layer chromatography on silica coated plates.

The substituted imine of the Formula III is then reacted with a suitable aldehyde or ketone reagent, herein defined as carbonyl reagents, to effect removal of the imino forming benzaldehyde or acetophenone to provide a 6-substituted-6-aminopenicillanic acid ester or a 7-substituted 7-aminocephalosporin ester represented by the Formula I wherein R is hydrogen.

The removal of the imine forming benzaldehyde or acetophenone is carried out by reacting the substituted imine in an inert solvent at a temperature between about 20° and 50° C. with a carbonyl reagent. Carbonyl reagents which can be employed in the above reaction include those reagents which are conventionally used to form derivatives of aldehydes and ketones such as sodium bisulfite, phenylhydrazine, phenylhydrazine p-sulfonic acid, Girard's reagent T (carboxymethyltrimethylammonium chloride hydrazide), Girard's reagent P (carboxymethylpyridinium chloride hydrazide), aminoxyacetic acid hemi hydrochloride, dimedone, and the like. The substituted imine esters can also be hydrolyzed under acid hydrolysis conditions as for example in methanolic or ethanolic hydrochloric acid. When the substituted β-lactam amino ester is prepared by acid hydrolysis the compound can be isolated in the form of the salt formed with the mineral acid employed in the hydrolysis, for example, the hydrochloride salt. Preferred reagents useful in the above reaction are Girard's reagent T and aminooxyacetic acid. Sodium bisulfite is used to advantage when the substituted imine is relatively impure. Generally a saturated or nearly saturated aqueous solution of sodium bisulfite is used. When an acidic aldehyde or ketone reagent such as phenylhydrazine p-sulfonic acid or aminoxyacetic acid is used, an equivalent of sodium acetate is desirably added to the reaction mixture to provide the non-acidic form of the reagent. The aldehyde or ketone reagent is employed in an amount equivalent to that of the substituted imine.

Solvents which can be employed in the present reaction include for example tetrahydrofuran, dioxane, water, and mixtures of the foregoing with the lower alcohols such as methanol and ethanol. The reaction generally proceeds at a satisfactory rate at room temperature. However, in certain instances the reaction mixture is best heated at a temperature slightly above room temperature, for example, between about 35° and 45° C.

The substituted amino ester nucleus is conveniently isolated from the reaction mixture in the form of an insoluble salt, for example, the p-toluenesulfonic acid salt or the α-naphthalene sulfonic acid salt. Such salts generally are obtained as crystalline solids.

The substituted amino-β-lactam ester compounds represented by the Formula I wherein R is hydrogen and $R_1$ is carboxy are prepared by reacting a 6-amino-6-(2,2,2-trichloroethoxycarbonyl)penicillanic acid ester, a 7-amino-7-(2,2,2-trichloroethoxycarbonyl)cephalosporanic acid ester or a 7-amino-7-(2,2,2-trichloroethoxycarbonyl)deacetoxycephalosporanic acid ester with zinc and formic acid or glacial acetic acid to effect cleavage or the trichloroethyl group and provide the free 6- or 7-carboxylic acid substituent group.

Alternatively and preferably the 6- or 7-(2,2,2-trichloroethoxycarbonyl)substituted amino-β-lactam ester is first acylated to provide the 6- or 7-acylamidopenicillin or cephalosporin ester which is thereafter reacted with zinc and formic acid to provide the 6-acylamido-6-carboxypenicillin or the 7-acylamido-7-carboxycephalosporin. Since the conditions for the cleavage of the $C_6$- or $C_7$- 2,2,2-trichloroethoxycabonyl substituent are the same as those required to effect the cleavage of the 2,2,2-trichloroethyl ester moiety at $C_3$- of a penicillin or $C_4$- of a cephalosporin; when $R_2$ in the Formula I represents the 2,2,2-trichloroethyl group, then both trichloroethyl groups can be removed simultaneously with zinc and formic acid or glacial acetic acid to provide in one cleavage step a 6-acylamido-6-carboxypenicillanic acid, a 7-acylamido-7-carboxycephalosporanic acid or a 7-acylamido-7-carboxydeacetoxycephalosporanic acid.

Illustrative of the substituted amino-β-lactam esters thus provided and which are represented by the Formula I wherein R is hydrogen, are the following:

p-nitrobenzyl 6-amino-6-acetylpenicillanate,
p-nitrobenzyl 6-amino-6-benzoylpenicillanate,
t-butyl 7-amino-7-n-propionylcephalosporanate,
benzyl 7-amino-7-pivaloyldeacetoxycephalosporanate,
2,2,2-trichloroethyl 7-amino-7-acetylcephalosporanate,
3,5-dimethoxybenzyl 7-amino-7-methoxymethylcephalosporanate,
2,2,2-trichloroethyl 6-amino-6-ethoxycarbonylpenicillanate,
benzyl 6-amino-6-n-propoxycarbonylpenicillanate,
p-nitrobenzyl 7-amino-7-n-butoxycarbonyldeacetoxycephalosporanate,
2,2,2-trichloroethyl 7-amino-7-methoxycarbonylcephalosporanate
2,2,2-trichloroethyl 7-amino-7-benzoyldeacetoxycephalosporanate,
p-nitrobenzyl 7-amino-7-acetyldeacetoxycephalosporanate,
2,2,2-trichloroethyl 7-amino-7-n-butyryldeacetoxycephalosporanate
2,2,2-trichloroethyl-6-amino-6-methoxymethylpenicillanate
2,2,2-trichloroethyl 7-amino-7-(2,2,2-trichloroethoxycarbonyl)deacetoxycephalosporanate,
2,2,2-trichloroethyl 7-amino-7-carboxydeacetoxycephalosporanate,
p-nitrobenzyl 6-amino-6-carboxypenicillanate,
2,2,2-trichloroethyl 7-amino-7-carboxycephalosporanate,
diphenylmethyl 7-amino-7-methoxycarbonylcephalosporanate,
diphenylmethyl 6-amino-6-ethoxycarbonylpenicillanate,
p-nitrobenzyl 7-amino-7-n-propoxycarbonylcephalosporanate,
p-nitrobenzyl 6-amino-6-(2,2,2-trichloroethoxycarbonyl)-penicillanate, and the acid addition salts thereof formed with p-toluenesulfonic acid and naphthalene sulfonic acid.

The free amino group of the above obtained acylated or methoxymethylated amino-β-lactam esters is then acylated with the desired acyl moiety according to procedures commonly practiced in the art to provide an acylamido penicillanic, cephalosporanic or deacetoxycephalosporanic acid of the Formula I wherein R is other than hydrogen. For example, the amino ester can be reacted with acyl halide, for example, acetyl chloride, phenoxyacetyl chloride, or 2-thienylacetyl chloride in an inert anhydrous solvent in the presence of a hydrogen halide accepting teritary amine such as pyridine or triethyl amine to provide the acylated penicillin or cephalosporin antibiotic compound. Alternatively, and also according to known methods, the amino ester can be acylated by reacting an acid with the amino group of the amino ester in the presence of a condensing agent such as dicyclohexylcarbodiimide. For example, phenoxyacetic acid can be reacted with the amino ester in the presence of dicyclohexylcarbodiimide under essentially anhydrous conditions to provide the phenoxyacetamido ester. The substituted amino esters can also be acylated according to the methods described in U.S. Pat. No. 3,502,664. Generally any of the acylation methods which have been employed in the acylation of 6-APA, 7-ACA, -nd 7-ADCA can be employed in the acylation of the 6- and 7-substituted derivatives thereof.

The ester group of the acylated compounds thus prepared is then removed by known methods to provide a 6-substituted 6-acylamidopenicillanic acid, a 7-substituted 7-acylamidocephalosporanic acid or a 7-substituted 7-acylamidodeacetoxycephalosporanic acid. For example, when $R_2$ in the Formula I is the 2,2,2-trichloroethyl group, the group is removed by the reaction of the ester with zinc in the presence of formic acid or acetic acid. When $R_2$ is benzyl or diphenylmethyl, the ester moiety can be removed under hydrogenolysis conditions in the presence of a catalyst such as palladium on carbon. The t-butyl ester can be removed by mild base hydrolysis. The 4-nitrobenzyl ester group can be removed either by catalytic hydrogenolysis in the presence of palladium on carbon or by mild acid hydrolysis.

In carrying out the preparation of the compounds of the Formula I according to the described process certain reactants and reaction conditions are preferred over others. The preferred imine forming aromatic carbonyl compound is p-nitrobenzaldehyde. Imines of 6-APA, 7-ACA and 7-ADCA formed with this aldehyde can usually be isolated as crystalline intermediates when the imine is prepared in ethanol, and such imines are formed in greater yields than those obtained with other aromatic aldehydes and acetophenones such as benzaldehyde and acetophenone.

Preferred carbonyl reagents employed in the removal of imine forming aldehydes or ketones are Girard's reagent T and aminooxyacetic acid hemi hydrochloride. Another preferred carbonyl reagent is sodium bisulfite employed as a saturated aqueous solution.

A preferred strong base is lithium diisopropyl amide.

A preferred ester of 6-APA, 7-ACA and 7-ADCA, as represented by $R_2$ in the Formulae I, II and III, is the 2,2,2-trichloroethyl ester.

In a preferred embodiment of the process of this invention, 2,2,2-trichloroethyl 7-aminodeacetoxycephalosporanate is reacted in ethanol with p-nitrobenzaldehyde and the imine, 2,2,2-trichloroethyl N-(p-nitrobenzylidene)-7-aminodeacetoxycephalosporanate formed thereby, is acylated in dry tetrahydrofuran with lithium diisopropyl amide and acetyl chloride to provide the 7-acetyl imine ester. The acetylated imine ester is then reacted with Girard's reagent T to effect the removal of the imine forming p-nitrobenzaldehyde, and to provide 2,2,2-trichloroethyl-7-amino-7-acetyl-deacetoxycephalosporanate. The latter amino-β-lactam ester is acylated with the desired acyl moiety, for example, 2-thienylacetyl chloride in ethyl acetate in the presence of pyridine to provide the compound represented by the Formula I, 2,2,2-trichloroethyl 7-[2'-(2-thienyl)acetamido]-7-acetyldeacetoxycephalosporanate. The acylated ester is then reacted with zinc and acetic acid to provide the deacetoxycephalosporanic acid.

The following compounds are illustrative of the penicillin and cephalosporin compounds provided by this invention as represented by the Formula I wherein R is other than hydrogen:

6-acetamido-6-acetylpenicillanic acid,
6-phenylacetamido-6-acetylpenicillanic acid
6-[2'-(2-thienyl)acetamido]-6-n-propionylpenicillanic acid,
6-phenoxyacetamido-6-acetylpenicillanic acid,
6-[2'-(2-furyl)acetamido]-6-benzoylpenicillanic acid,
6-benzamido-6-acetylpenicillanic acid, 6-(2,6-dimethoxybenzamido)-6-pivaloylpenicillanic acid,
6-(4-ethoxyphenylacetamido)-6-butyrylpenicillanic acid,
6-(4-chlorophenylacetamido)-6-acetylpenicillanic acid,
6-(3-hydroxyphenoxyacetamido)-6-acetylpenicillanic acid,
6-phenylmercaptoacetamido-6-methoxycarbonylpenicillanic acid,
6-acetamido-6-carboxypenicillanic acid,
6-(4-bromophenylacetamido)-6-isobutyrylpenicillanic acid,
6-(3,4-dichlorophenoxyacetamido)-6-acetylpenicillanic acid,
6-(4-bromophenylmercaptoacetamido)-6-ethoxycarbonylpenicillanic acid,
6-phenoxyacetamido-6-carboxypenicillanic acid,
6-[2'-(2-thienyl)acetamido]-6-carboxypenicillanic acid,
6-phenylmercaptoacetamido)-6-(2,2,2-trichloroethoxycarbonyl)penicillanic acid,
6-n-propionamido-6-benzoylpenicillanic acid,
6-[2'-(2-pyranyl)acetamido]-6-acetylpenicillanic acid,
6-[2'-(2-pyridylmercapto)acetamido]-6-carboxypenicillanic acid,
6-[2'-(2-thiazolyl)acetamido]-6-acetylpenicillanic acid,
6-butyramido-6-methoxymethylpenicillanic acid,
6-(3,4-dihydroxyphenylacetamido)-6-(2,2,2-trichloroethoxycarbonyl)penicillanic acid,
7-acetamido-7-benzoylcephalosporanic acid,
7-propionamido-7-acetylcephalosporanic acid,
7-phenoxyacetamido-7-n-butyrylcephalosporanic acid,
7-(3-hydroxyphenoxyacetamido)-7-propionyldeacetoxycephalosporanic acid,
7-phenylmercaptoacetamido-7-acetylcephalosporanic acid,
7-[2'-(2-thienyl)acetamido]-7-acetyldeacetoxycephalosporanic acid,
7-[2'-(2-pyridylmercapto)acetamido]-7-methoxycarbonyldeacetoxycephalosporanic acid,
7-[2'-(2-thiazolyl)acetamido]-7-benzoylcephalosporanic acid,
7[2'-(1,3,4-thiadiazo-2-yl)acetamido]-7-acetylcephalosporanic acid,
7-[2'-(3-thienyl)acetamido]-7-methoxycarbonyldeacetoxycephalosporanic acid,
7-phenoxyacetamido-7-(2,2,2-trichloroethoxycarbonyl)cephalosporanic acid,
7-phenoxyacetamido-7-carboxycephalosporanic acid,
7-phenoxyacetamido-7-carboxydeacetoxycephalosporanic acid,
7-[2'-(2-thienyl)acdtamido]-7-(2,2,2-trichloroethoxycarbonyl)cephalosporanic acid,
7-[2'-(2-thienyl)acetamido]-7-carboxycephalosporanic acid,
7-phenylacetamido-7-(2,2,2-trichloroethoxycarbonyl)deacetoxycephalosporanic acid,
7-phenylacetamido-7-carboxydeacetoxycephalosporanic acid,
7-[2'-(tetrazol-2-yl)acetamido]-7-acetylcephalosporanic acid,
7-propionamido-7-methoxymethylcephalosporanic acid,
7-butyramido-7-n-propoxycarbonyldeacetoxycephalosporanic acid,
7-valeramido-7-acetylcephalosporanic acid,
7-(2,6-dimethoxybenzamido)-7-methoxycarbonylcephalosporanic acid,
7-(4-hydroxybenzamido)-7-carboxydeacetoxycephalosporanic acid,
7-(2,6-dimethoxybenzyamido)-7-carboxycephalosporanic acid,
7-(4-hydroxyphenoxyacetamido)-7-n-propionylcephalosporanic acid,
7-phenylmercaptoacetamido-7-carboxydeacetoxycephalosporanic acid,
7-[2'-(2-triazinyl)acetamido]-7-acetylcephalosporanic acid,
7-(4-chlorophenylacetamido)-7-pivaloyldeacetoxycephalosporanic acid
7-phenoxyacetamido-7-pivaloylcephalosporanic acid,
7-(2'-amino-2'-phenylacetamido)-7-carboxydeacetoxycephalosporanic acid,
7-(2'-amino-2'-phenylacetamido)-7-(2,2,2-trichloroethoxycarbonyl)deacetoxycephalosporanic acid,
7-(2'-amino-2'-phenylacetamido)-7-methoxycarbonyldeacetoxycephalosporanic acid,
7-(2'-amino-2'-phenylacetamido)-7-acetyldeacetoxycephalosporanic acid,
7-(2'-hydroxy-2'-phenylacetamido)-7-acetyldeacetoxycephalosporanic acid,
7-(2'-amino-2'-phenylacetamido)-7-methoxymethyldeacetoxycephalosporanic acid, and The compounds of the Formula I wherein $R_1$ is $C_2$–$C_5$ alkanoyl, benzoyl, carboxy or methoxymethyl are useful antibiotic compounds which can be employed to inhibit the growth of microorganisms pathogenic to animal and plant life. The compounds of the Formula I wherein $R_1$ is a 2,2,2-trichloroethoxycarbonyl group are useful as intermediates in the preparation of the compounds where $R_1$ is a carboxy group as previously described.

The acylated and methoxymethylated β-lactam nuclei of the Formula 1 wherein R is hydrogen are useful intermediates for the preparation of the antibiotic compounds where R in Formula 1 is other than hydrogen.

The antibiotic activity of the compounds of the invention is illustrated by the data provided in the following Table I. The information contained in the table was obtained by employing the standard disc plate method. In the table R, Q and $R_1$ refer to the compounds represented by the following formula

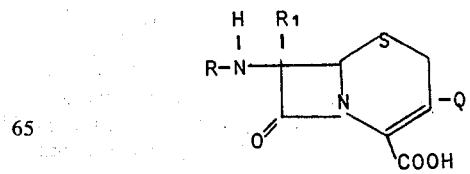

TABLE I

| Compound | | | Zone of Inhibition (diameter in mm)[1] | | | Concentration mg/ml |
|---|---|---|---|---|---|---|
| R | Q | $R_1$ | Staphylococcus aureus | Bacillus subtilis | Sarcina lutea | |
| phenoxyacetyl | $CH_3-$ | benzoyl | 21 | 22 | 18 | 1 |
| 2-thienylacetyl | $CH_3-$ | benzoyl | 23 | 22 | 19 | 1 |
| acetyl | $CH_3-$ | benzoyl | 14 | 12 | 15 | 20 |
| phenoxyacetyl | $CH_3COCH_2-$ (O=) | benzoyl | 25 | 29 | 22 | 1 |
| 2-thienylacetyl | $CH_3C(=O)-O-CH_2-$ | benzoyl | 17 | 20 | 15 | 1 |
| 2-thienylacetyl | $CH_3-$ | acetyl | 11 | — | 10 | 5 |
| 2-thienylacetyl | $CH_3-$ | methoxycarbonyl | 11 | 10 | — | 5 |
| 2-thienylacetyl | $CH_3-$ | carboxy | 15 | 15 | 13 | 1 |
| phenoxyacetyl | $CH_3-$ | carboxy | 16 | 16 | tr | 1 |
| acetyl | $CH_3-$ | carboxy | 9 | 21 | 19 | 20 |

[1] A dash indicated no observed zone of inhibition
tr indicates a trace zone of inhibition.

The β-lactam substituted penicillins and cephalosporins of this invention are relatively non-toxic substances which display acute $LD_{50}$ values in mice akin to those of the unsubstituted penicillin and cephalosporin antibiotics. The compounds described herein are particularly useful in combating infections caused by gram positive organisms.

It will be recognized by those skilled in the antibiotic art that the penicillanic acids, cephalosporanic acids and the deacetoxycephalosporanic acids provided by this invention will form salts with pharmaceutically acceptable bases. For example, the alkali metal or alkaline earth metal salts of these antibiotic acids can be prepared with such bases as sodium hydroxide, potassium hydroxide, sodium carbonate, sodium bicarbonate, potassium carbonate, calcium hydroxide and like bases. Such salts, for example the sodium and potassium salts likewise exhibit antibiotic activity and can be employed in suitable pharmaceutical formulations for combatting infections in warm blooded mammals.

The penicillins and cephalosporins represented by the Formula I, wherein $R_2$ is hydrogen, and the pharmaceutically acceptable salts thereof are useful in combatting infections in warm blooded mammals when administered parenterally at a dose between about 100 and 2,000 mg/kg. of body weight.

The following detailed examples are provided to further illustrate the present invention.

A. Preparation of the imine derivatives of 6-APA, 7-ACA and 7-ADCA esters.

EXAMPLE 1

2,2,2-Trichloroethyl N-(p-nitrobenzylidene-7-aminodeacetoxycephalosporanate

To a solution of 6.95 g. of 2,2,2-trichloroethyl 7-aminodeacetoxycephalosporanate in 50 ml. of absolute ethanol was added 2.3 g. of p-nitrobenzaldehyde. The reaction mixture was stirred at room temperature and after about 20 minutes the reaction product, 2,2,2-trichloroethyl N-(p-nitrobenzylidene)-7-aminodeacetoxycephalosporanate, precipitated from the reaction mixture as a crystalline solid. The precipitate was filtered and washed with ethanol to yield 7.83 g. of the imine ester product.

Elemental analysis calculated for $C_{17}H_{14}N_3O_5Cl_3$:

Calculated: C, 43.01%; H, 2.12%; N, 8.85%; O, 16.89%
Found: C, 42.92%; H, 2.23%; N, 9.08%; O, 16.56%
Infrared Absorption Spectrum in chloroform:
5.61μ (β-lactam carbonyl absorption)
Mass spectrum: $M^+477$, β-lactam scission 288.
Nuclear Magnetic Resonance Spectrum, δ($DCDl_3$)*:
2.23(3H,X,-$CH_3$); 3.26(H, d, 2H); 3.62(1H, d, 2-H); 4.86(1H, d,-$CO_2CH_3CCl_3$); 5.04(1H,d,-$CO_2CH_2CCl_3$);
5.26(1H,d,6H); 5.54(1H,m,7H);
8.13(4H,m,aromatic);

8.75(1H,d,—$\overset{H}{C}$=N—)

* s = singlet; d = doublet; m = multiplet.
Ultraviolet Absorption in ethanol: λ max. 2880 mμ (ε 19,100).

EXAMPLE 2

According to the procedure described by Example 1, 2,2,2-trichloroethyl 7-aminodeacetoxycephalosporanate was reacted with benzaldehyde in absolute ethanol to provide 2,2,2-trichloroethyl N-(benzylidene)-7-aminodeacetoxycephalosporanate having the following spectral characteristics:

Infrared Absorption Spectrum ($CHCl_3$): 5.63 μ (β-lactam carbonyl).
Ultraviolet Absorption Spectrum (EtOH): λ max. 253 mμ (ε 17,300).
Nuclear Magnetic Resonance spectrum λ ($CECl_3$):
2.18(3H,s,3-$CH_3$); 3.18(1H,d,2-H);
2.60(1H,d,2-H); 4.80(1H,d,-$CH_2CCl_3$);
5.05(1H,d,-$CH_2CCl_3$); 5.17(1H,d,6-H);
5.40(1H,m,7-H); 7.33-7.90(5H,m,aromatic);

8.62(1H,d,—$\overset{H}{C}$=N).

EXAMPLE 3

According to the procedure described by Example 1, 2,2,2-trichloroethyl 7-aminodeacetoxycephalosporanate was reacted in absolute ethanol with p-chlorobenzaldehyde to yield 2,2,2-trichloroethyl N-(p- chlorobenzylidene)-7-aminodeacetoxycephalosporanate having the following spectral characteristics:

Infrared Absorption Spectrum (CHCl$_3$): 5.63μ (β-lactam carbonyl).

Ultraviolet Absorption spectrum (EtOH): λ max. 262 mμ (ε 25,000)

Nuclear Magnetic Resonance spectrum, δ (CDCl$_3$)
2.40(3H,s,3-CH$_3$); 3.40(2H,AB quartet, 2-H);
4.92(2H,AB quartet,-CH$_2$CCl$_3$); 5.20(1H,d,6-H);
5.42(1H,m,7-H); 7.57(4H,AB quartet, aromatic);

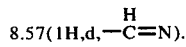
8.57(1H,d,—C=N).

EXAMPLE 4

According to the procedure described by Example 1, 2,4-dichlorobenzaldehyde was reacted in absolute ethanol with 2,2,2-trichloroethyl 7-aminodeacetoxycephalosporanate to provide 2,2,2-trichloroethyl N-(2,4-dichlorobenzylidene)-7-aminodeacetoxycephalosporanate having the following spectral properties:

Infrared Absorption spectrum (CCl$_4$):
5.68μ (β-lactam carbonyl);
6.20μ (—CH=N—)

Ultraviolet Absorption spectrum (EtOH): λ max. 263 mμ

Mass Spectrum: M$^+$ 502; β-lactam scission 288.

Nuclear Magnetic Resonance spectrum, δ (CDCl$_3$):
2.23(3H,s,3-CH$_3$); 3.45(2H, quartet, 2H);
4.93(2H,d,-CH$_2$CCl$_3$); 5.21(1H,d,6H);
5.47(1H,d fine splitting, 7H); 7.33, 2H,m,aromatic);
8.07(1H,d,aromatic); 8.97(1H,s fine splitting —CH=N—).

EXAMPLE 5 p-Nitrobenzaldehyde was reacted with p-nitrobenzyl 7-aminodeacetoxycephalosporanate according to procedures similar to those described by Example 1 to yield p-nitrobenzyl N-(p-nitrobenzylidene)-7-aminodeacetoxycephalosporanate having the following Nuclear Magnetic Resonance spectrum when run in deuterated dimethylsulfoxide (DMSO $d_6$)
2.05(3H,s,2-CH$_3$); 3.45(2H,AB quartet, 2-H);
5.27(1H,d,6-H); 5.33(2H,s,—CH$_2$—CCl$_3$);
5.65(1H,m,7-H); 7.52-8.40(8H,m,2 phenyl rings);

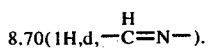
8.70(1H,d,—C=N—).

EXAMPLE 6

2,2,2-Trichloroethyl N-(α-methylbenzylidene)-7-aminodeacetoxycephalosporanate.

To a solution of 9.5 g. of 2,2,2-trichloroethyl 7-aminodeacetoxycephalosporanate in 50 ml. of absolute ethanol was added 3.33 g. of acetophenone. The reaction mixture was stirred at room temperature for 48 hours and the crystalline precipitate of the imine filtered. The precipitate was washed with petroleum ether and dried to give 8.5 g. of 2,2,2-trichloroethyl N-(α-methylbenzylidene)-7-amino-deacetoxycephalosporanate.

EXAMPLE 7

According to the procedure described by Example 6, p-nitroacetophenone was reacted in absolute ethanol with the trichloroethyl ester of 7-ADCA to provide the imine, 2,2,2-trichloroethyl N-(α-methyl-p-nitrobenzylidene)-7-aminodeacetoxycephalosporanate having the following spectral properties:

Infrared Absorption spectrum (CCl$_4$):
5.74μ (β-lactam carbonyl)
6.07μ (—CH=N—)

Ultraviolet absorption spectrum (EtOH): λ max. 280 mμ

Nuclear Magnetic Resonance spectrum, δ (CDCl$_3$):
2.20(3H,s,CH$_3$); 2.52(3H,s,-CH$_3$);
3.46(2H,q,-S-CH$_2$); 4.92(2H,d,O-CH$_2$);
5.21(1H,d,C$_6$-H); 5.65(1H,broad d, C$_7$-H);
8.11(4H,q,aromatic).

EXAMPLE 8

According to the procedure described by Example 1, 2,2,2-trichloroethyl 7-aminocephalosporanate was reacted in absolute ethanol with p-nitrobenzaldehyde to provide 2,2,2-trichloroethyl N-(p-nitrobenzyldene)-7-aminocephalosporanate having the following nuclear magnetic resonance spectrum in a mixture of deuterated dimethylsulfoxide and deuterated chloroform (DMSOd$_6$+CDCl$_3$).

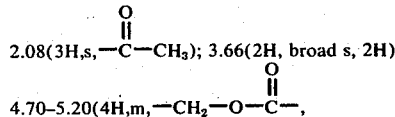

and -CH$_2$-CCl$_3$);
5.45(1H,d,6-H); 5.80(1H,m,7-H);
7.90-8.50(4H,m,aromatic);

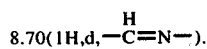
8.70(1H,d,—C=N—).

EXAMPLE 9

Following the procedure described by Example 1, the following imines were prepared with the indicated ester of 6-APA:

2,2,2-trichloroethyl N-(p-nitrobenzylidene)-6-aminopenicillinate having the following properties:

Elemental analysis calculated for C$_{17}$H$_{16}$N$_3$O$_5$SCl$_3$
Calculated: C, 42.47%; H, 3.35%; N, 8.74%; O,, 16.64%
Found: C, 42.26%; H, 3.13%; N, 8.99%; O, 16.82%

Infrared Absorption Spectrum (CDCl$_3$): 5.65 μ (β-lactam carbonyl)

Ultraviolet Absorption Spectrum (EtOH): λ max. 2.78 mμ (ε 16,000)

Nuclear Magnetic Resonance spectrum, δ (CDCl$_3$):
1.60 (3H,s,2-CH$_3$); 1.72(3H,s, 2-CH$_3$);
4.51(1H,s,3-H); 4.68(1H,d,-COOCH$_2$-CCl$_3$);
4.91(1H,d,COOCH$_2$CCl$_3$); 5.43 (1H,m,6-H);
5.69(1H,d,6-H); 8.09(4H,m,aromatic);

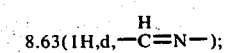
8.63(1H,d,—C=N—);

and, phenacyl N-(p-nitrobenzylidene)-6-aminopenicillanate having the following spectral properties:
Infrared Absorption spectrum (CHCl₃):
5.65 μ (β-lactam carbonyl)
6.10 μ (-CH=N-),

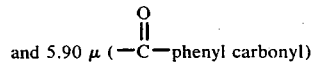

Ultraviolet Absorption Spectrum (EtOH):
λ max. 245 mμ (ε 17.700)
λ max. 275 mμ (ε 14.200)
Nuclear Magnetic Resonance spectrum, δ (CDCl₃):
1.74(6H(δ),-CH₃); 4.53(1H,s,C₃-H);
5.44(1H,q,C₅-H);

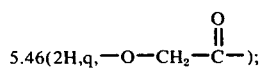

5.70(1H,d,C₆-H); 7.74(5H,m,aromatic);
8.11(4H,q,aromatic); 8.89(1H,d,-CH=N-).

B. ACYLATION OF IMINES.

EXAMPLE 10

2,2,2-Trichloroethyl 7-pivaloyl-N-(p-nitrobenzylidene)-7-aminodeacetoxycephalosporanate A solution of 4.78 g. of 2,2,2-trichloroethyl N-(p-nitrobenzylidene)-7-aminodeacetoxycephalosporanate in 65 ml. of dry DMF and 35 ml. of dry THF contained in a 3-necked round bottom flask equipped with a nitrogen inlet, a dropping funnel equipped with a drying tube, and a stopper was cooled in a dry ice-acetone bath to a temperature of about −78° C. Twenty milliliters of dry THF were added to the dropping funnel followed by 1.54 ml. of diisopropylamine and 6.8 ml. of a 1.6 molar solution of n-butyl lithium in hexane. The reactants in the dropping funnel were mixed well and allowed to cool. The cold contents of the dropping funnel were then run into the reaction solution of imine in the flask. After 10 minutes 5.3 g. of pivaloyl chloride were added to the reaction mixture. After 2 hours and 40 minutes the reaction mixture was diluted with an acidic solution of sodium chloride (acidified with hydrochloric acid) and the diluted mixture was extracted 3 times with 500 ml. portions of ethyl acetate. The extracts were combined and successively washed with acidic sodium chloride solution, 20% sodium bicarbonate solution, and a 50% sodium chloride solution. The extract was then dryed and evaporated to a dry residue of the crude reaction product 2,2,2-trichloroethyl 7-pivaloyl-N-(p-nitrobenzylidene)-7-aminodeacetoxycephalosporanate. The product was purified by dissolving the crude compound in dichloromethane and adding the solution dropwise to hexane. The dichloromethane was evaporated from the solution and the precipitate filtered on a cotton plug. The precipitate was redissolved in dichloromethane and the solution was diluted with a mixture of ether-hexane to precipitate the product. The above precipitation procedure was repeated 3 times to obtain 2.7 g. of the purified product.

EXAMPLE 11

2,2,2-Trichloroethyl 7-acetyl-N-(p-nitrobenzylidene)-7-aminodeacetoxycephalosporanate In a dry, 250 ml. 3-necked round bottom equipped with a nitrogen inlet, a stopper and a dropping funnel attached to a drying tube was added a solution of 4.78 g. of 2,2,2-trichloroethyl N-(p-nitrobenzylidene)-7-aminodeacetoxycephalosporanate in a mixture of 65 ml. of dry DMF and 35 ml. of dry THF. The solution was cooled to −80° C. in an acetone-dry ice bath. A solution lithium diisopropyl amide in 20 ml. of THF (prepared in the dropping funnel with 7.88 ml. of n-butyl lithium and 1.54 ml. of diisopropylamine) was added to the cold solution. After 10 min. 3.45 g. of freshly distilled acetyl chloride was added rapidly to the mixture. The reaction mixture was stirred in the cold for 30 min. and was then extracted with 3,500 ml. portions of ethyl acetate. The extract was washed 4 times with an acidic solution of sodium chloride and twice with a neutral solution of sodium chloride and was dried over sodium sulfate. The dried extract was evaporated to dryness and the residue dissolved in methylene dichloride. Hexane was added to the solution to form a precipitate. The methylene dichloride was evaporated and the remaining hexane solution was filtered on a cotton plug. The precipitate on the plug was redissolved in methylene dichloride and ether was added to precipitate the product. The methylene dichloride was evaporated from the solution and hexane was added to the concentrate. Next the ether was evaporated and the hexane solution filtered to obtain 4.15 g. of the purified reaction product, 2,2,2-trichloroethyl 7-acetyl-N-(p-nitrobenzylidene)-7-aminodeacetoxycephalosporanate as confirmed by the nmr, infrared, U.V. and mass spectra of the product.

EXAMPLE 12

2,2,2-Trichloroethyl 6-benzoyl-N-(p-nitrobenzylidene)-6-aminopenicillanate.

Following the acylation procedures described in Example 11, 4.8 g. of 2,2,2-trichloroethyl N-(p-nitrobenzylidene)-6-aminopenicillanate was reacted with lithium diisopropyl amide and 2.81 g. of benzoyl chloride in dry DMF-THF to yield 4.04 g. of 2,2,2-trichloroethyl 6-benzoyl-N-(p-nitrobenzylidene)-6-aminopenicillanate.

EXAMPLE 13

2,2,2-Trichloroethyl 7-benzoyl-N-(p-nitrobenzylidene)-7-aminodeacetoxycephalosporanate To a solution of 4.78 g. of 2,2,2-trichloroethyl N-(p-nitrobenzylidene)-7-aminodeacetoxycephalosporanate in a dry mixture of 70 ml. of DMF and 30 ml. of THF maintained under nitrogen at −48° C. was added an oil dispersion of sodium hydride (625 mg. of sodium hydride) and the blue mixture was stirred for 90 min. after addition was complete. To the mixture was added 1.83 g. of benzoyl chloride and the mixture was stirred for 30 min. The blue color of the iminesodium hydride mixture faded immediately on addition of the halide. The reaction mixture was diluted with 200 ml. of ethyl acetate and 250 ml. of an acidic sodium chloride solution. The organic layer was separated and was washed first with an acidic solution of sodium chloride and then with a solution of sodium bicarbonate. The washed ethyl acetate layer was dried and evaporated to dryness. The residue was dissolved in methylene chloride and the solution diluted with hexane to precipitate the crude reaction product contaminated with starting material. The reaction product was separated from the starting material by preparative thin layer chromatography to yield the purified product.

EXAMPLE 14

2,2,2-Trichloroethyl 6-(2,2,2-trichloroethoxycarbonyl)-N-(p-nitrobenzylidene)-6-aminopenicillanate Following the acylation procedure described in Example 10, 4.80 g. of 2,2,2-trichloroethyl N-(p-nitrobenzylidene)-6-aminopenicillanate was reacted in a dry mixture of DMF and THF with lithium diisopropyl amide and 9.3 g. 2,2,2-trichloroethyl chloroformate to yield in 54.5 percent 2,2,2-trichloroethyl 6-(2,2,2-trichloroethoxycarbonyl)-N-(p-nitrobenzylidene)-6-aminopenicillanate as confirmed by the NMR, infrared, U.V. and mass spectra of the reaction product.

EXAMPLE 15

2,2,2-Trichloroethyl 7-(2,2,2-trichloroethoxycarbonyl)-N-(p-nitrobenzylidene)-7-aminodeacetoxycephalosporanate.

Following the acylation procedure of Example 10, 9.5 g. of 2,2,2-trichloroethyl N-(p-nitrobenzylidene)-7-aminodeacetoxycephalosporanate was reacted with lithium diisopropyl amide and 2,2,2-trichloroethyl chloroformate to provide 10.65 g. of 2,2,2-trichloroethyl 7-(2,2,2-trichloroethoxycarbonyl)-N-(p-nitrobenzylidene)-7-aminodeacetoxycephalosporanate.

EXAMPLE 16

Following the acylation procedure described in Example 10, 5.36 g. of 2,2,2-trichloroethyl N-(p-nitrobenzylidene)-7-aminocephalosporanate was reacted with lithium diisopropyl amide and 9.3 g. of trichloroethyl chloroformate to yield 5.88 g. of 2,2,2-trichloroethyl 7-(2,2,2-trichloroethoxycarbonyl)-N-(p-nitrobenzylidene)-7-aminocephalosporanate.

EXAMPLE 17

2,2,2-Trichloroethyl 7-methoxycarbonyl-N-(p-nitrobenzylidene)-7-aminodeacetoxycephalosporanate Following the acylation procedure described in Example 10, 4.78 g. of 2,2,2-trichloroethyl N-(p-nitrobenzylidene)-7-aminodeacetoxycephalosporanate was reacted with lithium diisopropyl amide and 4.15 g. of methyl chloroformate to yield 3.81 g. of the 7-methoxycarbonyl product as shown by the NMR, infrared, U.V. and mass spectra of the isolated product.

C. PREPARATION OF 7-AMINO-7-SUBSTITUTED β-LACTAM ESTERS AND THE ACYLATION THEREOF.

EXAMPLE 18

2,2,2-Trichloroethyl 7-acetyl-7-aminodeacetoxycephalosporanate

To a solution of 520 mg. of 2,2,2-trichloroethyl 7-acetyl-N-(p-nitrobenzylidene)-7-aminodeacetoxycephalosporanate in 10 ml. of methanol and 5 ml. of methylene chloride was added 0.2 ml. of a 23% solution of hydrochloric acid in methanol. The mixture was stirred at room temperature for 100 min. and another 0.2 ml. of methanol —HCl was added. After 3.5 hours the reaction mixture was evaporated to dryness and the residue was dissolved in methylene chloride. The solution was diluted with hexane to precipitate the crude reaction product. The solution-precipitation process was repeated three times to afford the crude reaction product as a yellow solid insoluble in hexane. The crude product was dissolved in ethyl acetate and the solution was extracted with dilute hydrochloric acid and with a dilute solution of sodium bicarbonate. The aqueous extracts were combined and were washed with twice with ethyl acetate. The organic washes were combined and dried. Evaporation of the dried organic layer gave 323 mg. of 2,2,2-trichloroethyl 7-acetyl-7-aminodeacetoxycephalosporanate.

EXAMPLE 19

7-Acetyl-7-[2-(2-thienyl)acetamido]deacetoxycephalosporanic acid.

To a solution of 323 mg. of 2,2,2-trichloroethyl 7-acetyl-7-aminodeacetoxycephalosporanate, prepared as described in Example 18, in 15 ml. of acetonitrile maintained at −45° C. was added 240 mg. of 2-thienylacetyl chloride and 0.16 ml. of pyridine. After one hour, the reaction mixture was diluted with ethyl acetate and with hydrochloric acid. The ethyl acetate layer was separated and was washed with dilute hydrochloric acid and with a dilute solution of sodium bicarbonate. The washed ethyl acetate layer was dried and evaporated to yield 480 mg. of crude product. The product was purified by dissolution in methylene chloride followed by precipitation with hexane. The solution-precipitation procedure was repeated twice to afford 404 mg. of the purified product. The product was recrystallized from ethyl acetate, melting at about 200°–201° C. with decomposition.

The above prepared ester was dissolved in 5 ml. of a 2:1 mixture of DMF:acetic acid and the solution was cooled in an ice bath. Zinc dust, 200 mg., was added to the solution with stirring. After 2 hours the mixture was filtered to remove zinc which was washed on the filter with ethyl acetate and with water. The aqueous layer of the filtrate was separated from the organic layer and the organic layer was washed with water. The organic layer was then extracted with a dilute solution of sodium bicarbonate and the acidic reaction product recovered from the extract by acidification and extraction with ethyl acetate. The ethyl acetate extract was dried and evaporated to dryness to yield the 96.5 mg. of 7-acetyl-7-[2′-(2-thienyl)acetamido]deacetoxycephalosporanic acid. The product was recrystallized from ethyl acetate chloroform.

EXAMPLE 20

2,2,2-Trichloroethyl 7-amino-7-benzoylcephalosporanate.

To a solution of 642 mg. of 2,2,2-trichloroethyl 7-benzoyl-N-(p-nitrobenzylidene)-7-aminocephalosporanic acid in a mixture of 15 ml. of THF and 5 ml. of methanol was added 218.6 mg. of aminooxyacetic acid hemi hydrochloride and the reaction mixture was stirred at room temperature for 90 min. The reaction mixture was extracted with ethyl acetate and the extract was washed with a diluted hydrochloric acid solution and a 50% aqueous solution of sodium bicarbonate. The washed solution was dried and evaporated to yield 459.4 mg. of 7-amino-7-benzoylcephalosporanic acid trichloroethyl ester.

EXAMPLE 21

Following the procedure described in Example 20, 4.31 g. of 2,2,2-trichloroethyl 7-benzoyl-N-(p-nitrobenzylidene)-7-aminodeacetoxycephalosporanate was reacted with 1.62 g. of aminoxyacetic acid hemi hydrochloride to provide the free amino β lactam ester which was isolated as the p-toluenesulfonic acid salt. There was obtained 2.29 g. of the salt melting at about 152°–154° C.

EXAMPLE 22

Following the procedure described in Example 20, 2,2,2-trichloroethyl 6-benzoyl-N-(p-nitrobenzylidene)-6-aminopenicillanate was reacted with aminooxyacetic acid hemi hydrochloride to provide 2,2,2-trichloroethyl 6-amino-6-benzoylpenicillanate.

EXAMPLE 23

Following the imine hydrolysis procedures employing aminooxyacetic acid hemi hydrochloride described in Example 20 the following compounds were prepared. In each instance the starting material was the N-(p-nitrobenzylidene) derivative.

2,2,2-trichloroethyl 7-amino-7-methoxycarbonyldeacetoxycephalosporanate, 2,2,2-trichloroethyl 6-amino-6-(2,2,2-trichloroethoxycarbonyl)penicillanate, 2,2,2-trichloroethyl 7-amino-7-(2,2,2-trichloroethoxycarbonyl)deacetoxycephalosporanate p-toluenesulfonate salt melting at about 180°–182° C.

2,2,2-trichloroethyl 7-amino-7-acetylcephalosporanate,

EXAMPLE 24

7-Carboxy-7-phenoxyacetamidodeacetoxycephalosporanic acid.

To a solution of 2,2,2-trichloroethyl 7-amino-7-(2,2,2-trichloroethoxycarbonyl)deacetoxycephalosporanate, obtained from 693.3 mg. of the p-toluenesulfonate salt, in 25 ml. of methylene chloride was added 0.44 ml. of triethylamine and the mixture was cooled to −80° c. To the cold mixture was added 304 mg. of phenoxyacetyl chloride in methylene chloride. The reaction mixture was allowed to warm to −40° c. and an additional 340 mg. of phenoxyacetyl chloride and 0.3 ml. of triethylamine were added. When thin layer chromatography indicated little acylated product an additional 340 mg. of phenoxyacetyl chloride and 0.16 ml. of pyridine were added to the mixture. Thin layer chromatography then indicated the reaction was complete. Methanol was added to the reaction mixture followed by a solution of sodium chloride acidified with hydrochloric acid. The mixture was extracted with ethyl acetate and the extract was washed with dilute hydrochloric acid and with a dilute solution of sodium bicarbonate. The extract was dried and evaporated to obtain the crude reaction product. The crude product was purified by repeated precipitation from a methylene chloride solution induced by dilution with hexane to provide 744 mg. of the purified, 2,2,2-trichloroethyl 7-phenoxyacetamido-7-(2,2,2-trichloroethoxycarbonyl)deacetoxycephalosporanate.

The product was dissolved in 10 ml. of a 2:1 mixture of DMF:glacial acetic acid and 1.4 g. of zinc dust were added. The reaction mixture was stirred at room temperature for 2 hours. The mixture was filtered and the filter was washed with ethyl acetate and dilute hydrochloric acid. The ethyl acetate layer of the filtrate was separated and washed with dilute hydrochloric acid and then dried over sodium sulfate. The dried extract was evaporated to dryness and the residue dissolved in methylene chloride. The reaction product was precipitated from the solution by the addition of hexane or diisopropyl ether.

The product was dissolved in ethyl acetate and was extracted with a solution of sodium bicarbonate. The bicarbonate extract was acidified to pH 1.5 and was then extracted with ethyl acetate. The extract was dried and evaporated to yield 294.8 mg. of 7-carboxy-7-phenoxyacetamidodeacetoxycephalosporanic acid.

EXAMPLE 25

6-Phenylthioacetamido-6-ethoxycarbonylpenicillanic acid is prepared by reacting benzyl 6-amino-6-ethoxycarbonylpenicillanate with phenylmercaptoacetyl chloride in the presence of triethylamine and removing the benzyl ester group of the product, benzyl 6-phenylthioacetamido-6-ethoxycarbonylpenicillanate by catalytic hydrogenolysis over 5% palladium on carbon.

EXAMPLE 26

7-[2′-(2-Oxazol-2-yl)acetamido]-7-methoxymethyldeacetoxycephalosporanic acid is prepared by reacting the substituted amino-β-lactam ester, 3,5-dimethoxybenzyl 7-amino-7-methoxymethyldeacetoxycephalosporanate with 2-Oxazolylacetyl chloride in the presence of pyridine and removing the ester group by catalytic hydrogenolysis over 5% palladium on carbon.

EXAMPLE 27

7-[2′-(1-tetrazolyl)acetamido]-7-acetylcephalosporanic acid is prepared by the reaction of p-nitrobenzyl 7-amino-7-acetylcephalosporanate with 1-tetrazolylacetyl chloride in the presence of triethylamine and removing the p-nitrobenzyl ester group of the product.

EXAMPLE 28

7-Carboxy-7-phenylthioacetamidocephalosporanic acid is prepared by reacting 2,2,2-trichloroethyl 7-amino-7-(2,2,2-trichloroethoxycarbonyl)cephalosporanate with phenylmerceptoacetyl chloride in the presence of pyridine to provide 2,2,2-trichloroethyl 7-phenylthioacetamido-7-(2,2,2-trichloroethoxycarbonyl)cephalosporanate and reacting the latter compound with zinc and acetic acid to cleave both trichloroethyl groups.

EXAMPLE 29

7-[2′-(2-Imidazolyl)acetamido]-7-acetylcephalosporanic acid is prepared by reacting 2,2,2-trichloroethyl 7-acetyl-7-aminocephalosporanate with 2-imidazolylacetyl chloride in the presence of triethylamine and removing the trichloroethyl ester group by reacting the product with zinc and acetic acid.

We claim:

1. A compound of the formula

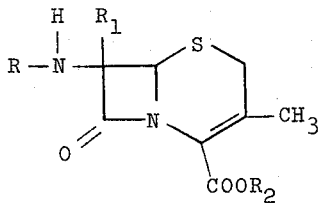

wherein R is hydrogen or an acyl group selected from the group consisting of $C_2$–$C_7$ alkanoyl, thienylacetyl and furylacetyl; $R_1$ is carboxy or 2,2,2-trichloroethoxycarbonyl and $R_2$ is hydrogen or 2,2,2-trichloroethyl.

2. The compound of claim 1 said compound being 7-carboxy-7-[2'-(2-thienyl)acetamido]deacetoxycephalosporanic acid.

3. A compound of claim 1 wherein R is hydrogen.

* * * * *